(12) United States Patent
Mittelstadt et al.

(10) Patent No.: US 8,936,596 B2
(45) Date of Patent: Jan. 20, 2015

(54) METHOD AND APPARATUS FOR GENERATING A TOOL PATH FOR A ROBOTIC ORTHOPEDIC SURGICAL PROCEDURE

(76) Inventors: Brent Mittelstadt, Pollock Pines, CA (US); Youngbae Park, Fremont, CA (US)

( * ) Notice: Subject to any disclaimer, the term of this patent is extended or adjusted under 35 U.S.C. 154(b) by 16 days.

(21) Appl. No.: 13/529,721

(22) Filed: Jun. 21, 2012

(65) Prior Publication Data

US 2013/0035690 A1 Feb. 7, 2013

Related U.S. Application Data

(60) Provisional application No. 61/499,572, filed on Jun. 21, 2011.

(51) Int. Cl.
- A61B 17/00 (2006.01)
- A61B 17/17 (2006.01)
- G06K 9/36 (2006.01)
- G06T 7/00 (2006.01)
- A61B 17/16 (2006.01)
- A61B 19/00 (2006.01)
- G06F 19/00 (2011.01)

(52) U.S. Cl.
CPC . *A61B 17/17* (2013.01); *G06K 9/36* (2013.01); *G06T 7/0012* (2013.01); *A61B 17/1626* (2013.01); *A61B 19/50* (2013.01); *G06F 19/3437* (2013.01); *G06F 19/3481* (2013.01); *A61B 19/2203* (2013.01); *A61B 2017/1602* (2013.01); *A61B 2019/505* (2013.01); *A61B 2019/507* (2013.01)
USPC .......................................... 606/79; 606/86 R (58) Field of Classification Search
CPC .......................... A61B 19/50; A61B 2017/568
USPC ................................ 606/79, 82, 86 R, 87–89
See application file for complete search history.

(56) References Cited

U.S. PATENT DOCUMENTS

| 5,824,085 A | 10/1998 | Sahay et al. |
| 6,033,415 A * | 3/2000 | Mittelstadt et al. ........... 606/130 |

\* cited by examiner

*Primary Examiner* — Andrew Yang
(74) *Attorney, Agent, or Firm* — Pandiscio & Pandiscio (57) ABSTRACT

A method for generating an improved tool path for cutting a bone so as to minimize soft tissue trauma, wherein the method comprises:
accessing an image of the bone which is to be cut;
accessing an image of a pre-determined cutting pattern;
superimposing the image of the pre-determined cutting pattern against the image of the bone;
calculating the intersection of the pre-determined cutting pattern and the bone using the superimposed images of the pre-determined cutting pattern and the bone; and
generating a tool path based upon the intersection of the pre-determined cutting pattern and the bone so as to minimize soft tissue trauma by leaving a thin perimeter of bone at the boundary of the bone cut when the boundary of the bone cut is adjacent to a bone surface.

18 Claims, 12 Drawing Sheets

METHOD AND APPARATUS FOR GENERATING A TOOL PATH FOR A ROBOTIC ORTHOPEDIC SURGICAL PROCEDURE

REFERENCE TO PENDING PRIOR PATENT APPLICATION

This patent application claims benefit of pending prior U.S. Provisional Patent Application Ser. No. 61/499,572, filed Jun. 21, 11 by Brent Mittelstadt for TOOL PATH GENERATION METHOD FOR A ROBOTIC ORTHOPEDIC PROCEDURE, which patent application is hereby incorporated herein by reference.

FIELD OF THE INVENTION

This invention relates to pre-operative surgical planning software for robotic orthopedic surgical procedures, and more particularly to a novel method and apparatus for producing a patient-specific tool path for shaping bone during a robotic orthopedic surgical procedure.

BACKGROUND OF THE INVENTION

In an orthopedic surgical procedure which requires the cutting or shaping of bone, achieving higher accuracy in cutting or shaping the bone can yield superior surgical outcomes. To this end, orthopedic surgical robots such as the ROBODOC® surgical assistant system (Curexo Technology Corp., Fremont, Calif., USA) have been developed. These orthopedic surgical robots utilize computer-controlled surgical cutters which allow superior accuracy to be achieved in the cutting or shaping of bone.

With the current ROBODOC® system, the surgeon uses, prior to surgery, pre-operative surgical planning software to plan the intended position of the implant vis-à-vis the bone. More particularly, CT scan data is processed so as to provide a virtual model of the bone, an implant library is provided which comprises virtual models of the various implants available to the surgeon, and the pre-operative surgical planning software allows the virtual model of the implant to be merged with the virtual model of the bone so as to enable the surgeon to visualize the final implant position vis-à-vis the bone, and so as to enable the surgeon to see the tool path which will be used by the surgical robot to cut the bone so that the bone can properly receive the implant.

By way of example but not limitation, U.S. Pat. No. 5,824,085 discloses a system which may be used for pre-operative surgical planning. This system accepts a virtual model of the bone which is to receive the implant. This virtual model of the bone is typically generated using CT scan data of the bone. The system also stores a library of virtual models of the implants which are available to the surgeon. Using the pre-operative surgical planning system, the surgeon can superimpose the virtual model of the implant on the virtual model of the bone so as to visualize, prior to the actual surgery, the final position of the actual implant vis-à-vis the actual bone. The pre-operative surgical planning system also shows the tool path which will be used by the surgical robot to cut the bone to receive that implant. Thereafter, after the surgical robot and the bone have been placed into proper registration with one another, the surgical robot can automatically cut the bone according to the planned data, so that the bone can properly receive the implant.

However, the bone which is to receive the implant is typically surrounded by soft tissue such as muscles, tendons, blood vessels, nerves, skin, etc. During the orthopaedic surgery, care should be taken to preserve those soft tissues. Among other things, and of special concern with respect to the present invention, during the cutting of the bone, the cutting tool (e.g., the saw blade or high-speed rotating cutter) should not damage the soft tissues located beyond the bone, i.e., by penetrating beyond the bone. By way of example but not limitation, in total hip replacement surgery and/or in total knee replacement surgery, it is important to avoid damaging soft tissue structures (e.g., delicate neurovascular structures) which lie adjacent to the bones being cut.

To prevent such soft tissue damage during the cutting of bone, several approaches has been used in manual surgical procedures. For example, a curved metal protector is sometimes slid between the bone and the soft tissue so as to protect the soft tissue from the cutting tool. Or, a "plunging cutter" (or drill) can be equipped with a physical stop mechanism or depth gauge so that the surgeon does not inadvertently cut beyond the boundary of the bone.

Figure 1A:
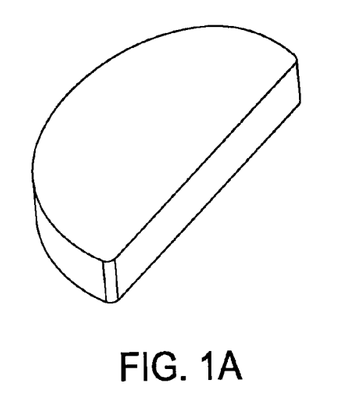
FIGS. 1A-1D are schematic views showing a tibial implant of a unicondylar knee and its toolpath, with FIG. 1A being an orthogonal view of the implant, FIG. 1B being a top view of the implant, FIG. 1C being a top view of the tool path for the implant which requires a surgical opening of width L, and FIG. 1D showing possible tissue damage if the implant is larger than the bone.
Figure 1B:
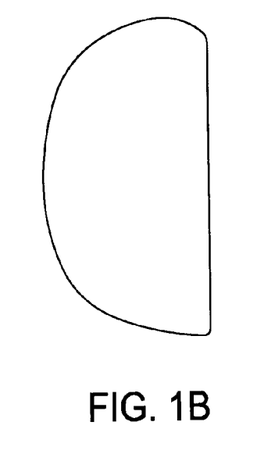
Figure 1C:
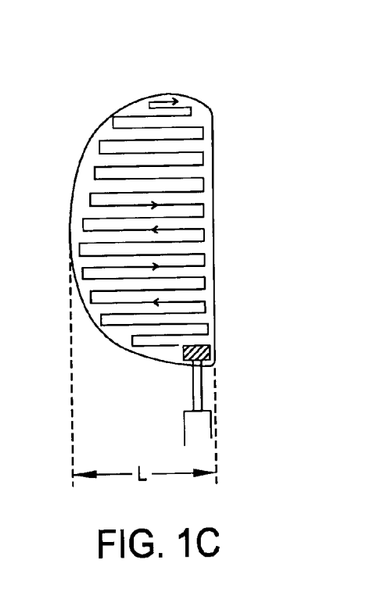
Figure 1D:
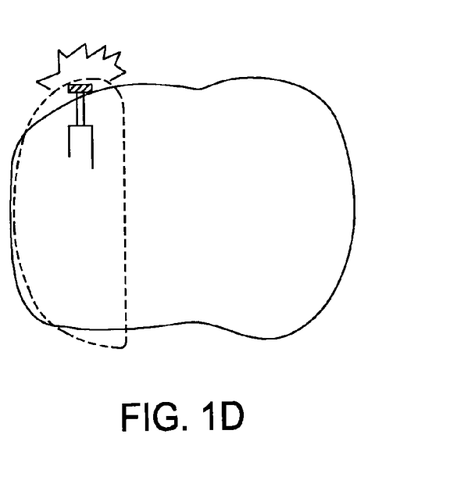

Using a robotically-controlled cutting tool, it is possible to achieve precise cutting accuracy when cutting the bone. In order to achieve optimum cutting accuracy with minimized cutting time, it is desirable for the tool path, and the feed rate of the cutting tool, to be pre-programmed. At the same time, however, inasmuch as each bone has a unique shape for each patient, the pre-programmed tool path should be customized for each patient. By way of example but not limitation, if the pre-programmed tool path is not customized for each patient, there is the possibility that the bone may be overcut. More particularly, if the planned implant volume extends outside the bone, then the surgical robot's cutter moves beyond the outer boundary of the bone and will engage any anatomical structures located within the planned implant volume. Thus, the cutter can cause damage to soft tissue (or other anatomical structures) surrounding the bone. See, for example, FIGS. 1A-1D, which are schematic views showing a tibial implant (FIGS. 1A and 1B), the pre-defined tool path for the tibial implant, which requires a surgical opening of width L (FIG. 1C), and possible soft tissue damage where the implant is larger than the patient's bone (FIG. 1D).

Moreover, inasmuch as the surgical opening used during the operation may vary in size, shape and/or location, the direction of approach of the tool path should take into account the nature of the surgical opening so that movement of the surgical robot does not collide with the perimeter of the surgical opening. Also, as mentioned above, the robotic cutting should ensure that the cutting does not damage soft tissue adjacent to the bone. At the same time, the use of conventional metal protectors, which is common in manual surgery, is problematic in robotic surgery because, if the cutter collides with the metal protector, the cutter and protector may be damaged and may leave metal debris in the patient's body. Furthermore, during typical robotic surgery, there is generally insufficient room to accommodate a metal protector due to the presence of the robot tool or robot arm.

Thus, there is a need for a new method and apparatus for generating an improved tool path for an implant which minimizes soft tissue trauma, e.g., by utilizing a pre-determined tool path but also protecting the soft tissues behind or around the bone, and also minimizing the required surgical access.

SUMMARY OF THE INVENTION

The present invention provides a novel method and apparatus for generating an improved tool path for an implant which minimizes soft tissue trauma, e.g., by utilizing a pre-determined tool path but also protecting the soft tissues behind or around the bone, and also minimizing the required surgical access.

In accordance with the present invention, this is done by accessing an image of the bone which is to be cut and accessing an image of the desired cut (i.e., the pre-determined cutting pattern) which is to be made in the bone. The pre-determined cutting pattern is a combination of the volume or surface which will be cut by the surgical robot, as well as containing a template of the pre-determined tool path for that volume or surface. The image of the cutting pattern is placed over the image of the bone. Then the intersection of the cutting pattern and the bone is calculated. Based upon this intersection, a tool path is generated to cut the bone in the cutting pattern, with the tool path being designed to minimize soft tissue damage, e.g., by reducing bone overcut, and/or by reducing the size of the surgical opening which is made to access the bone, and/or by leaving a thin perimeter of bone at the boundary of the bone cut when the boundary of the bone cut is adjacent to a bone surface. Preferably the aforementioned image of the bone is provided by a virtual model of the bone, and the aforementioned image of the pre-determined cutting pattern is provided via a virtual model of the pre-determined cutting pattern.

More particularly, during tool path generation, the tool path may be optimized based on the surgical access, which may be defined during the surgery or prior to the surgery. Moreover, the excessive tool path (i.e., the tool path which extends beyond the perimeter of the bone) is "trimmed" (i.e., abbreviated) so that the surgical robot does not cut the beyond the boundary of the bone. Furthermore, the tool path can be optimized so as to reduce the size of the surgical opening used to access the bone. In addition, during the trimming and the optimization of the tool path, the tool path can be generated so that a thin perimeter of bone is left after completion of the cutting so that the thin perimeter of bone can act as a protective wall to prevent contact of the cutting tool with the soft tissue located beyond the bone. Inasmuch as robotically-controlled cutters are capable of high degrees of precision, having an accuracy greatly superior to manual tools, the thickness of the thin perimeter of bone can be sub-millimeter (e.g., 0.8 mm) if desired.

Once the optimized tool path has been determined, the optimized tool path is loaded into an orthopedic surgical robot and is used to cut the bone which is to receive the implant.

In one preferred form of the invention, there is provided a method for generating an improved tool path for cutting a bone so as to minimize soft tissue trauma, wherein the method comprises:

accessing an image of the bone which is to be cut;
accessing an image of a pre-determined cutting pattern;
superimposing the image of the pre-determined cutting pattern against the image of the bone;
calculating the intersection of the pre-determined cutting pattern and the bone using the superimposed images of the pre-determined cutting pattern and the bone; and
generating a tool path based upon the intersection of the pre-determined cutting pattern and the bone so as to minimize soft tissue trauma by leaving a thin perimeter of bone at the boundary of the bone cut when the boundary of the bone cut is adjacent to a bone surface.

In another preferred form of the invention, there is provided a method for cutting bone, the method comprising:
accessing an image of the bone which is to be cut;
accessing an image of a pre-determined cutting pattern;
superimposing the image of the pre-determined cutting pattern against the image of the bone;
calculating the intersection of the pre-determined cutting pattern and the bone using the superimposed images of the pre-determined cutting pattern and the bone;
identifying a preferred surgical access prior to or during the surgery; and
generating a tool path based upon the intersection of the pre-determined cutting pattern and the bone which accesses the bone through the preferred surgical access and leaves a thin perimeter of bone at the boundary of the bone cut when the boundary of the bone cut is adjacent to a bone surface, except for where the tool needs to approach and cut the bone from the preferred surgical access.

In another preferred form of the invention, there is provided apparatus for generating an improved tool path for cutting a bone so as to minimize soft tissue trauma, wherein the method comprises:
means for accessing an image of the bone which is to be cut;
means for accessing an image of a pre-determined cutting pattern;
means for superimposing the image of the pre-determined cutting pattern against the image of the bone;
means for calculating the intersection of the pre-determined cutting pattern and the bone using the superimposed images of the pre-determined cutting pattern and the bone;
means for generating a tool path based upon the intersection of the pre-determined cutting pattern and the bone so as to minimize soft tissue trauma by leaving a thin perimeter of bone at the boundary of the bone cut when the boundary of the bone cut is adjacent to a bone surface.

In another preferred form of the invention, there is provided apparatus for cutting bone, the apparatus comprising:
means for accessing an image of the bone which is to be cut;
means for accessing an image of a pre-determined cutting pattern;
means for superimposing the image of the pre-determined cutting pattern against the image of the bone;
means for calculating the intersection of the pre-determined cutting pattern and the bone using the superimposed images of the pre-determined cutting pattern and the bone;
means for identifying a preferred surgical access prior to or during the surgery; and
means for generating a tool path based upon the intersection of the pre-determined cutting pattern and the bone which accesses the bone through the preferred surgical access and leaves a thin perimeter of bone at the boundary of the bone cut when the boundary of the bone cut is adjacent to a bone surface, except for where the tool needs to approach and cut the bone from the preferred surgical access.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

The present invention provides a novel method and apparatus for generating an improved tool path for an implant which minimizes soft tissue trauma, e.g., by utilizing a pre-determined tool path but also protecting the soft tissues behind or around the bone, and also minimizing the required surgical access.

Figure 2:
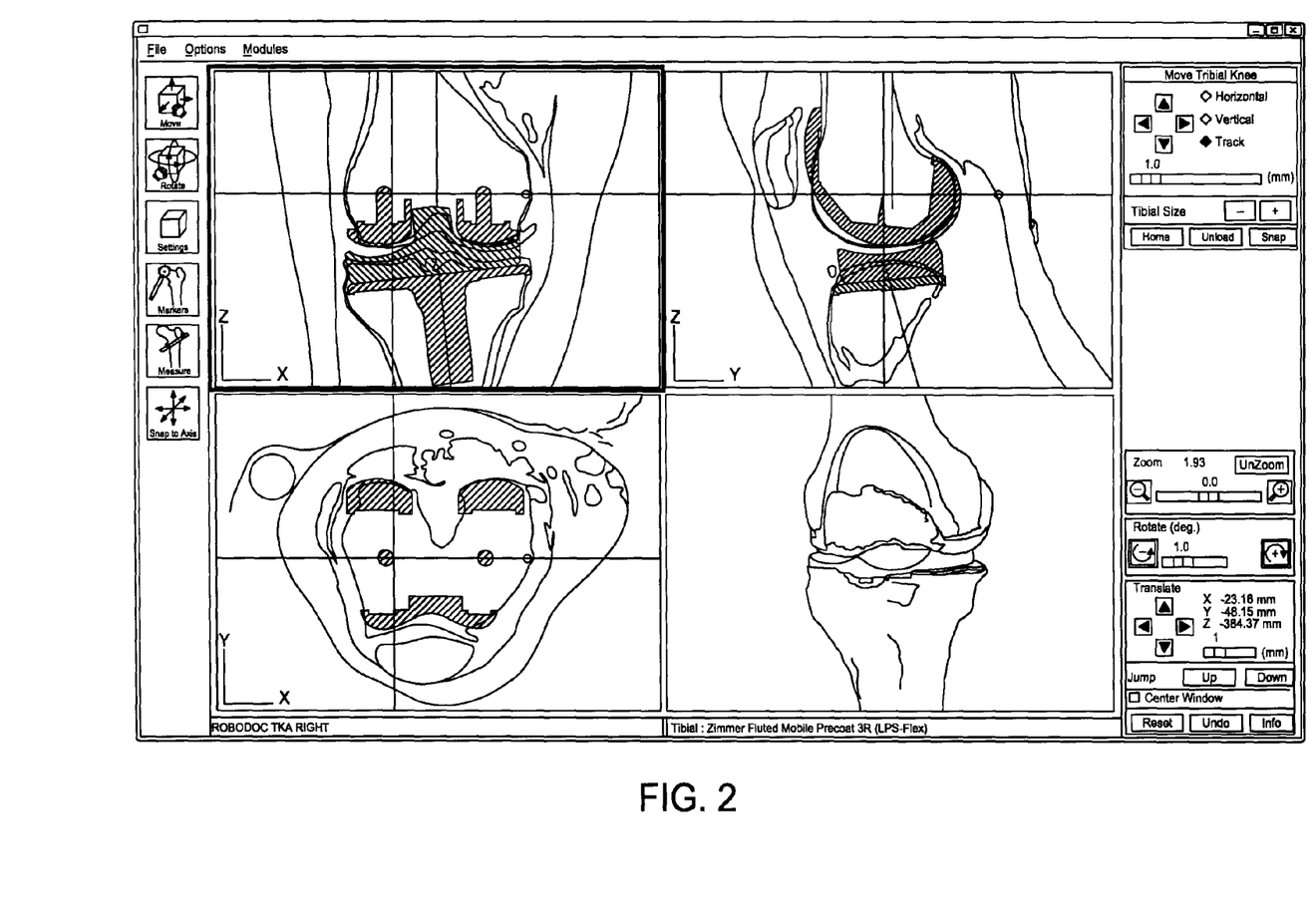
FIG. 2 is a schematic view showing the pre-operative surgical planning software of the present invention.

In accordance with the present invention, this is done by using pre-operative surgical planning software (FIG. 2) to access an image of the bone which is to be cut and to access an image of the desired cut (i.e., the pre-determined cutting pattern) which is to be made in the bone. The pre-determined cutting pattern is a combination of the volume or surface which will be cut by the surgical robot, as well as containing a template of the pre-determined tool path for that volume or surface. The image of the cutting pattern is placed over the image of the bone. Then the intersection of the cutting pattern and the bone is calculated. Based upon this intersection, a tool path is generated to cut the bone in the cutting pattern, with the tool path being designed to minimize soft tissue damage, e.g., by reducing bone overcut and/or by reducing the size of the surgical opening which is made to access the bone, and/or by leaving a thin perimeter of bone at the boundary of the bone cut is adjacent to a bone surface. Preferably the aforementioned image of the bone is provided by a virtual model of the bone, and the aforementioned image of the pre-determined cutting pattern is provided via a virtual model of the pre-determined cutting pattern.

More particularly, during tool path generation, the tool path may be optimized based on the surgical access, which may be defined during the surgery or prior to the surgery. Moreover, the excessive tool path (i.e., the tool path which extends beyond the perimeter of the bone) is "trimmed" (i.e., abbreviated) so that the surgical robot does not cut beyond the boundary of the bone. Furthermore, the tool path can be optimized so as to reduce the size of the surgical opening used to access the bone. In addition, during the trimming and optimization of the tool path, the tool path can be generated so that a thin perimeter of bone is left after completion of the cutting so that the thin perimeter of bone can act as a protective wall to prevent contact of the cutting tool with the soft tissue located beyond the bone. Inasmuch as robotically-controlled cutters are capable of high degrees of precision, having an accuracy greatly superior to manual tools, the thickness of the thin perimeter of bone can be sub-millimeter (e.g., 0.8 mm) if desired.

Figure 3:
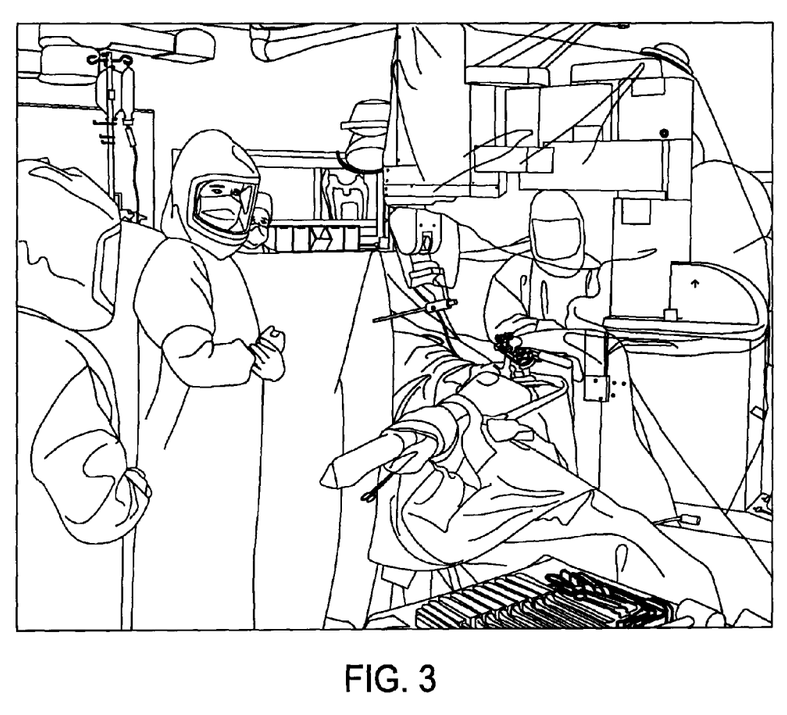
FIG. 3 is a schematic view showing an orthopedic surgical robot with high-speed surgical cutter which may be used in accordance with the present invention.
Figure 4:
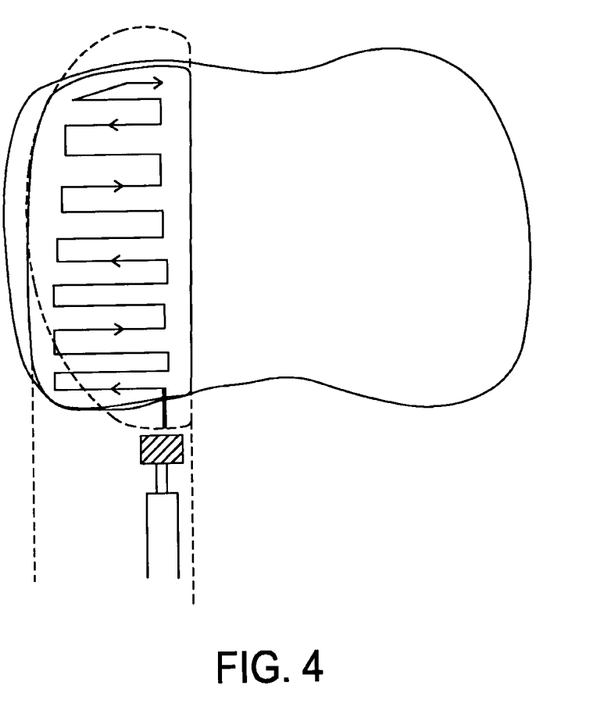
FIG. 4 is a schematic view showing an optimized tool path designed to ensure that the cutter cuts only the required amount of bone.
Figure 5A:
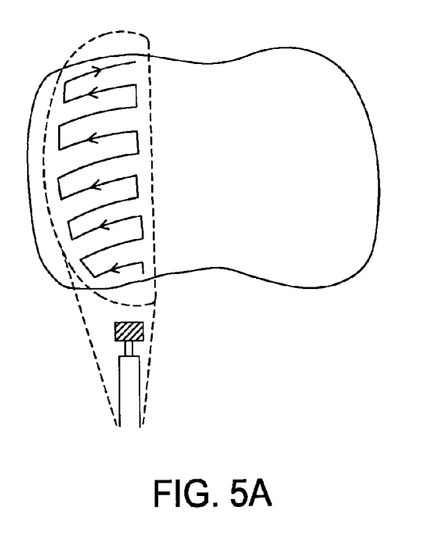
FIGS. 5A and 5B are schematic views showing optimized tool paths designed to minimize the size of the surgical incision which must be made to access the bone, with FIG. 5A showing optimization for a medial incision and FIG. 5B showing optimization for a more lateral incision.
Figure 5B:
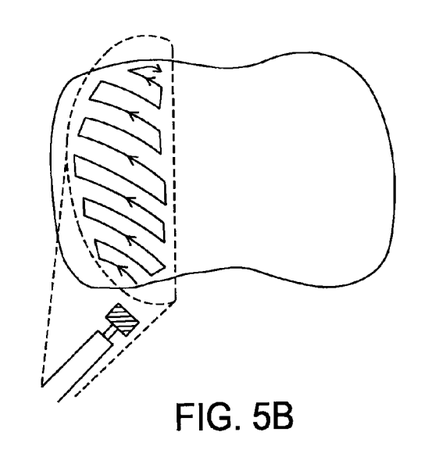

Once this optimized tool path has been determined, the optimized tool path is loaded into an orthopedic surgical robot (FIG. 3) and is used to cut the bone which is to receive the implant. Among other things, the optimized tool path can reduce bone overcut (FIG. 4) and/or reduce the size of the surgical opening which is made to access the bone (FIGS. 5A and 5B), and/or leave a thin perimeter of bone at the boundary of the bone cut when the boundary of the bone cut is adjacent to a bone surface so as to protect soft tissue located beyond the bone.

The improved tool path is preferably generated as follows.

1. Medical Image of the Bone and Tissue.

Figure 6:
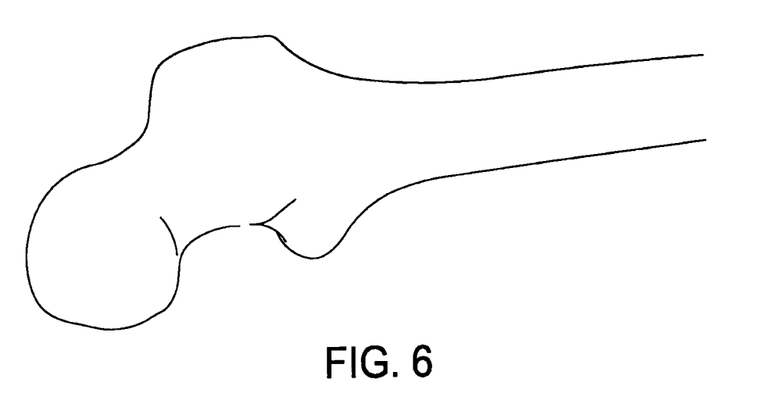
FIG. 6 is a schematic view showing the proximal end of a femur.

First, a CT scan of the relevant patient anatomy is obtained. By way of example but not limitation, the CT scan may be of a proximal femur which requires an osteotomy below the lesser trochanter (FIG. 6).

2. Pre-processing of the Medical Image.

The CT image is processed so that bone is segmented from soft tissue. The segmented bone information may be stored as a virtual model (e.g., a polygonal surface model or a solid model) of the sort well known in the art.

3. Cutting Pattern Library.

Figure 7A:
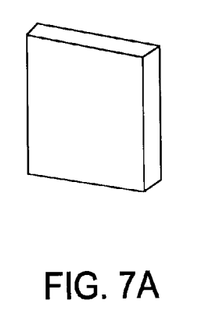
FIGS. 7A-7C are schematic views illustrating a library of pre-determined cutting patterns, with FIG. 5A showing a plane cut, FIG. 5B showing a wide V-cut and FIG. 5C showing a sharp V-cut.
Figure 7B:
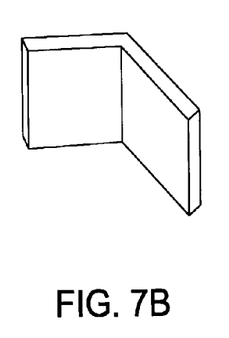
Figure 7C:
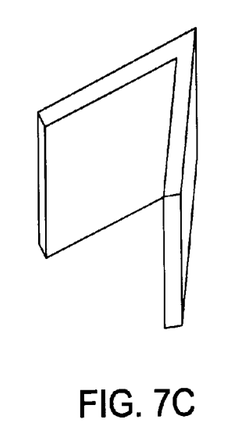

In the pre-operative surgical planning software, there is provided a library of pre-defined cutting patterns. FIG. 7 shows several possible cutting patterns. Note that due to the thickness of the cutting tool, even for a simple planar osteotomy, the cutting pattern should have a thickness. Preferably the pre-defined cutting patterns are stored as virtual models (e.g., a polygonal surface model or a solid model) of the sort well known in the art. Also, the pre-determined cutting pattern may include the pre-defined tool path which defines preferred feed (i.e., direction of approach, feed rate, etc.) and other cutting variables so that the cutting can be performed in a controlled and accurate manner. The pre-defined tool path can be further optimized by software which "trims" unnecessary cutting (i.e., eliminates unnecessary cutting) and/or adjusts the tool approach and/or leaves a thin perimeter of bone at the boundary of the bone cut when the boundary of the bone cut is adjacent to a bone surface so as to protect soft tissue located beyond the bone.

4. Planning.

Figure 8:
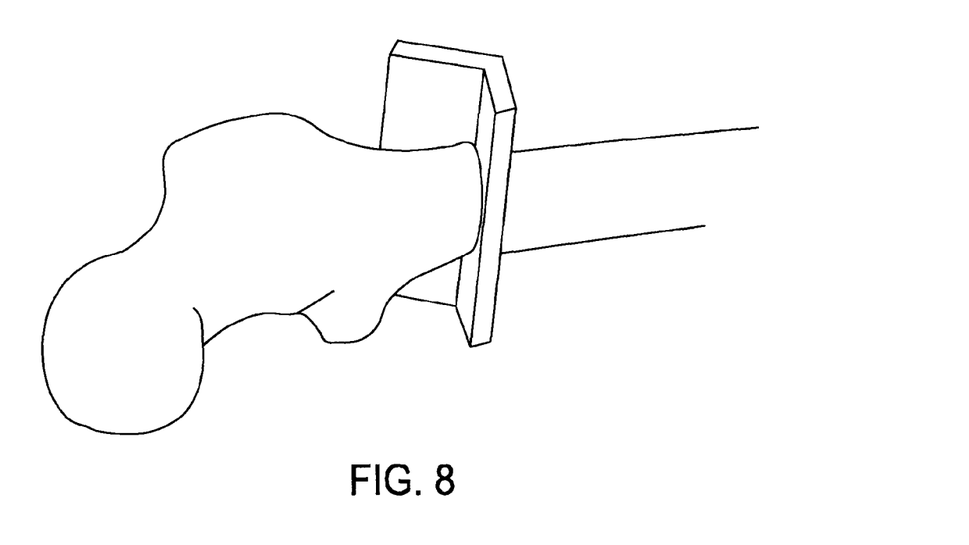
FIG. 8 is a schematic view showing the superimposition of an image of a wide V-cut cutting pattern over the image of the bone.

The virtual model of the bone is accessed by the pre-operative surgical planning software. Using the pre-operative surgical planning software, the surgeon can view the virtual model of the patient's bone. Also, the surgeon can select a pre-defined cutting pattern from the library of pre-defined cutting patterns and superimpose that cutting pattern on the virtual model of the patient's bone. See FIG. 8, which shows the placement of a V-cut to the femur (i.e., the placement of a V-cut cutting pattern on the virtual model of the bone). Again, the pre-defined cutting pattern is preferably stored as a virtual model, so superimposing the pre-defined cutting pattern on the virtual model of the patient's bone essentially involves superimposing one virtual object (e.g., the pre-defined cutting pattern) on another virtual object (e.g., the virtual model of the bone).

During the pre-operative surgery, and as discussed in further detail below, the surgeon may also input the preferred surgical access as the surgeon plans how the incision will be made and how the bone will be accessed.

5. Identifying Volume to be Removed.

Figure 9:
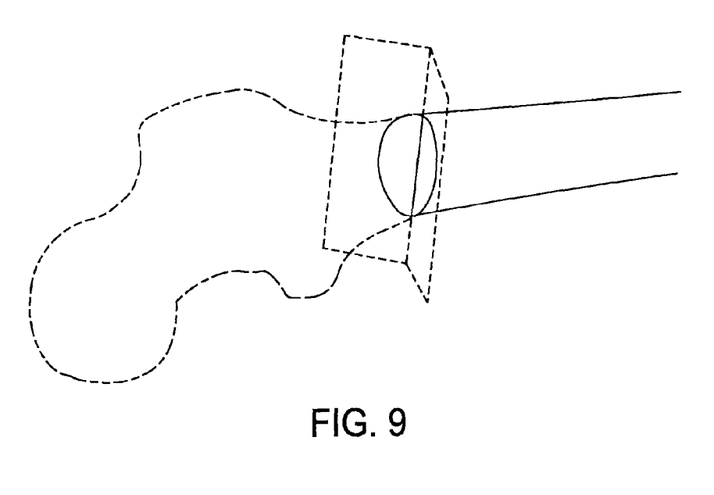
FIG. 9. is a schematic view showing the expected shape of the distal femur after an osteotomy using the wide V-cut cutting pattern shown in FIG. 8.

Using the segmented bone information and the cutting pattern information, the intersection of the cutting volume and the patient bone can be calculated. By way of example but not limitation, FIG. 9 shows the expected shape of the distal femur if the surgeon cuts the bone according to the proposed cut of FIG. 8 (i.e., the bone cut proposed by the superimposition of the cutting pattern on the virtual model of the bone).

Figure 10:
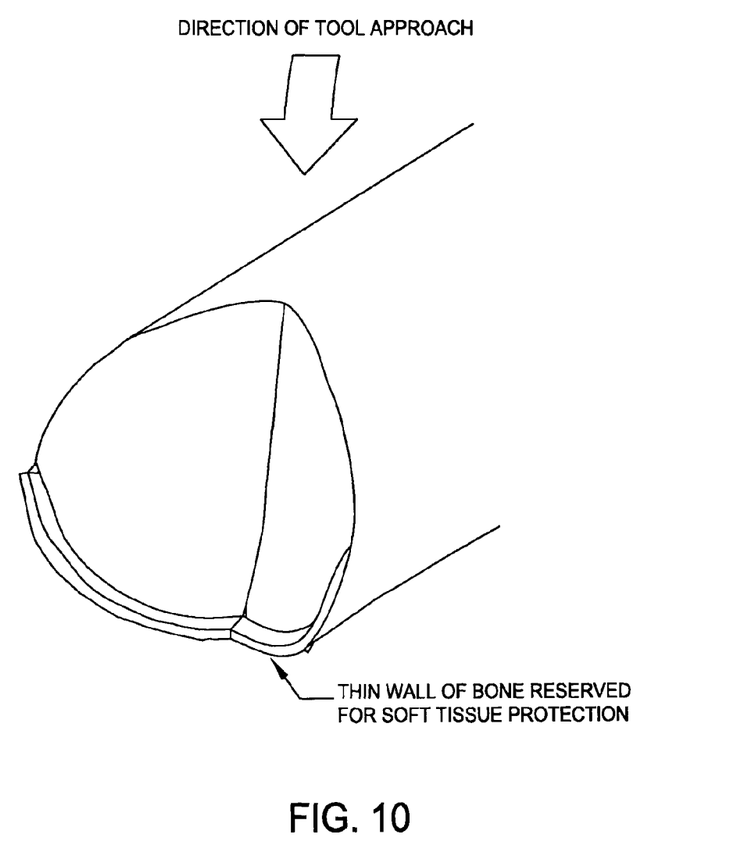
FIG. 10 is a schematic view showing surgeon preferences for the wide V-cut osteotomy of the distal femur.

Also, during this planning stage, and as noted above, the surgeon can set several preferences. For example, the surgeon may wish to specify an angle of approach from the lateral side of the patient (FIG. 10). Or the surgeon may wish to leave a thin wall of bone (i.e., a thin perimeter of bone) on the far side of the bone, i.e., on the side of the bone opposite to the surgical opening (FIG. 10). The provision of this thin wall of bone provides an additional measure of safety for the patient, as it will protect the soft tissue on the far side of the bone (which is not easily visible to the surgeon during the robotic cutting). This thin wall of bone can be easily removed manually with an appropriate osteotome after the robotic cutting is completed.

6. Tool Path Optimization.

Figure 11:
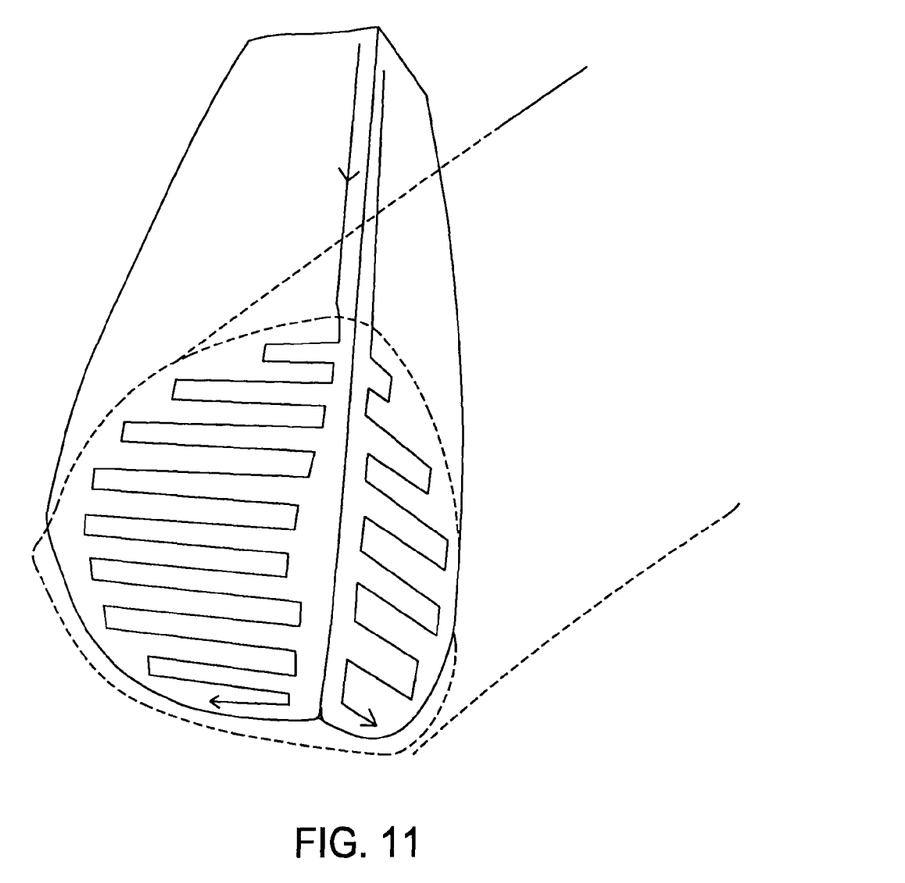
FIG. 11 is a schematic view of the generated tool path for the wide V-cut osteotomy of the distal femur.

Once the volume of bone which is to be removed has been determined, as well as the direction of approach of the cutter, then the tool path can be generated for this volume (FIG. 11).

During the tool path generation, the tool path can be optimized. Various algorithms can be used to optimize the tool path according to the priorities of the user. By way of example but not limitation, an algorithm may be used which minimizes the possibility of overcutting the bone. Or an algorithm may be used which minimizes the size of the surgical opening needed for the tool path. Or an algorithm may be used which minimizes the time required for bone cutting. Or an algorithm may be used which provides the most accurate bone cutting with a particular cutting tool. It will be appreciated that these and other algorithms will be apparent to those skilled in the art in view of the present disclosure.

By way of example but not limitation, the possibility of overcutting the bone may be minimized by comparing the intersection of the virtual model of the cutting pattern with the virtual model of the bone and eliminating any portion of the cutting pattern which lies outside of the bone.

By way of further example but not limitation, the surgical opening (which is defined as the size of the opening through the soft tissue which is required for the cutting tool to access and cut bone) can be minimized by the following algorithm.

Pseudocode For Tool Path Optimization, Where the Size of the Surgical Opening is to be Minimized For a high-speed rotary cutter which has a long cylindrical tool shape, the size of the surgical opening can be minimized as follows:

(1) Define a position, $P_0$, which is the center of the surgical opening. This position $P_0$ may be defined during the surgery by using a user interface, or by using a digitizer, or the position $P_0$ may be pre-defined prior to the surgery.

(2) For a given tool position at a time t, let the tool center position be $P(t)$ and let the directional vector of the long axis of the tool be $V(t)$. Then calculate distance $d(t)$ as follows:

$$d(t)=|P_0-P(t)-(P_0-P(t))\cdot V(t)/|V(t)||$$

where the $\cdot$ means vector dot and $||$ means vector norm.

(3) The optimized tool path is that which minimizes the maximum $d(t)$ over the entire time.

7. Verification by Visualization.

Once the tool path has been determined, the tool path (and the tool movement) can be shown to the surgeon for visual verification.

8. Tool Path Generation.

After the tool path has been visually verified by the surgeon, the tool path is saved and then uploaded to the surgical robot for use in the surgery.

9. Surgery.

Thereafter, the surgical robot uses the tool path generated above to automatically cut bone. Due to the manner by which the tool path was generated, soft tissue trauma is reduced, e.g., by reducing bone overcut, by reducing the size of the surgical opening which is made to access the bone, and/or by leaving a thin perimeter of the bone at the boundary of the bone cut when the boundary of the bone cut is adjacent to a bone surface so as to protect soft tissue located beyond the bone.

Flowchart

Figure 12:
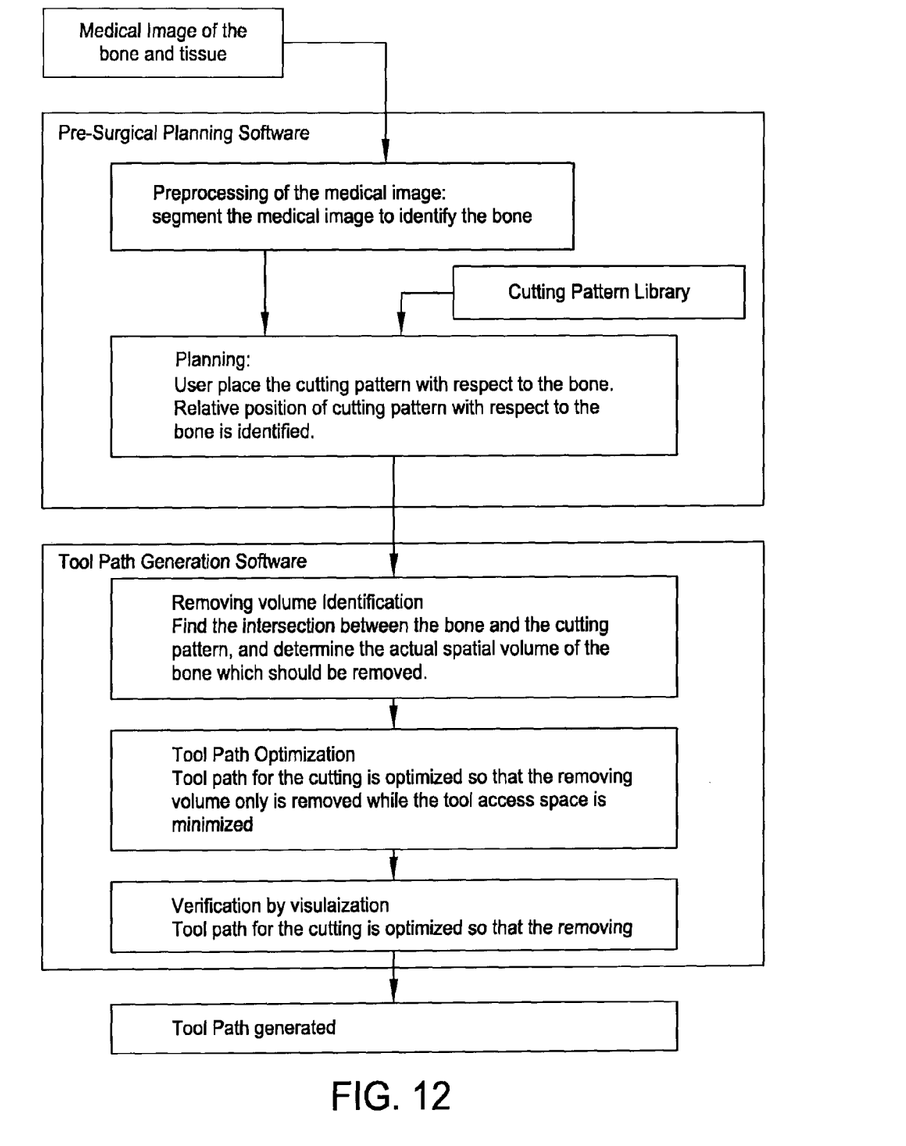
FIG. 12 is a flowchart showing the process for generating the patient-specific tool path.

FIG. 12 is a flowchart showing the steps used in generating the optimized tool path.

Further Exemplary Embodiments Of The Present Invention

Medical Image of the Bone and Tissue

In the foregoing description, a CT scan is used to generate a virtual model of the patient's anatomy. However, other 3D medical imaging modalities can also be used to generate a virtual model of the patient's anatomy, e.g., MRI, 3D fluoroscopy, etc.

Furthermore, it is possible to utilize medical imaging modalities other than 3D medical imaging modalities to generate a virtual model of the patient's anatomy, e.g., more than one planar X-ray image can be used to generate a virtual model of the patient's anatomy.

Additionally, it is possible to use a virtual model which is not generated by a medical imaging modality. By way to example but not limitation, a parametric model of the patient's bone can be used. For purposes of the present description, a parametric model of the bone is intended to mean a generic bone model which is pre-defined, but which can be modified (e.g., enlarged or distorted) so as to have dimensions similar to the patient's actual bone.

Pre-processing of the Medical Image

The medical image is pre-processed so that bone is segmented from soft tissue. As noted above, the medical image can be pre-processed so as to create a virtual model of the anatomy, with the virtual model being a polygonal surface model or a solid model. Alternatively, the segmented bone information can be stored as voxel data, with the bone being segmented from the soft tissue by selecting the voxels of CT data which have a density value higher than a certain threshold value (i.e., so as to distinguish bone from soft tissue).

Cutting Pattern Library

In the foregoing description, the pre-operative surgical planning software was described as including a library of pre-defined implants (e.g., hip implants, knee implants, ankle implants, shoulder implants, etc.) and pre-defined cutting patterns. In this respect it should be appreciated that the libraries of pre-defined cutting patterns and/or pre-defined implants can be imported from various CAD software programs, and may be in various formats (e.g., IGES, STEP, STL, etc.) so as to provide for the use of patient-specific custom implants and/or for the use of allograft implants.

Planning

In the planning phase, the image of the bone is transferred to the pre-operative surgical planning software. In the pre-operative surgical planning software, the surgeon can visually observe the patient's bone. This visualization can be done in a 3D modality and/or in one or more 2D projections (e.g., on slice images of the patient's anatomy).

Identifying Volume to be Removed

From the segmented bone information and the cutting pattern information, an intersection of the cutting volume and the patient bone can be calculated.

Tool Path Optimization

Instead of generating the tool path in the pre-operative surgical planning software, the cutting pattern library can include pre-defined tool paths for each cutting pattern in the library, and these pre-defined tool paths can be optimized by:

removing any unnecessary portions of the tool path, so as to prevent bone overcut; and/or adding additional portions to the pre-defined tool path, so as to access the complete cutting space; and/or optimizing the direction of insertion of the cutting tool, so as to reduce the size of the required surgical opening.

Verification by Visualization

Visual verification of the cutting path during the pre-operative planning stage can be omitted. Or, the visual verification can be conducted in the operating room. Or, the verification can be done physically by the surgical robot before the surgery.

Tool Path Generation

The tool path generation software can be installed on the surgical robot itself, thus the tool path does not need to be generated pre-operatively (e.g., using the pre-operative surgical planning software) and then transferred to surgical robot.

Also, the cutting tool can comprise a tool other than a high-speed rotary burr, e.g., it can be a oscillating surgical saw, a high-energy waterjet, a bone ablation laser, etc. In each case, an appropriate change should be made to the algorithm generating the tool path.

Some Significant Aspects of the Present Invention

1. The tool path is generated based on the relative positions of 2 pre-defined shapes (i.e., the patient's bone and the cutting pattern).

2. The tool path, which is pre-generated for the most efficient cut for a given implant, is compared to the location of the bone cut, and that portion of the cutting path which is not within the bone is removed so that the surgical robot cuts only bone.

3. The tool path which is pre-generated for the most efficient cut can be modified intraoperatively, so that the surgical robot does not cut bone where the surgeon thinks cutting is unnecessary.

4. The tool path is generated and optimized, so as to minimize the required surgical opening.

5. The tool path can provide for a thin perimeter of bone to be left during the robotic cutting, with the thin perimeter of bone acting as a protector to prevent the exposure of the soft tissue behind or around the bone to be cut.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A method for generating an improved tool path for cutting a bone so as to minimize soft tissue trauma, wherein the method comprises:

accessing an image of the bone which is to be cut;

accessing an image of a pre-determined cutting pattern;

superimposing the image of the pre-determined cutting pattern against the image of the bone;

calculating the intersection of the pre-determined cutting pattern and the bone using the superimposed images of the pre-determined cutting pattern and the bone; and generating a tool path based upon the intersection of the pre-determined cutting pattern and the bone so as to minimize soft tissue trauma by leaving a thin perimeter of bone at the boundary of the bone cut when the boundary of the bone cut is adjacent to a bone surface;

wherein the tool path is generated to provide for tool access which complies with the surgical access which is defined by user input during the surgery; and wherein sizing of a surgical opening is reduced according to the following algorithm:

(1) Define a position, $P_0$, which is the center of the surgical opening:

(2) For a given tool position at a time t, let the tool center position be $P(t)$ and let the directional vector of the long axis of the tool be $V(t)$, then calculate distance $d(t)$ as follows:

$$d(t)=|P_0-P(t)-(P_0-P(t)) \cdot V(t)/|V(t)||$$

where the · means vector dot and | | means vector norm:

(3) The optimized tool path is that which minimizes the maximum $d(t)$ over the entire time.

2. A method according to claim 1 wherein the pre-determined cutting pattern is associated with an implant which is to be placed into the bone.

3. A method according to claim 1 wherein the tool path is generated to leave a thin perimeter of bone except where required for tool access.

4. A method according to claim 1 wherein the image of the bone is provided via a virtual model of the bone.

5. A method according to claim 4 wherein the virtual model of the bone is generated from CT data.

6. A method according to claim 1 wherein the image of the pre-determined cutting pattern is provided by a virtual model of the pre-determined cutting pattern.

7. A method according to claim 1 wherein the tool path takes into account an angle of approach specified by the surgeon.

8. A method according to claim 1 wherein the tool path takes into account surgeon-specified boundaries beyond which the bone is not to be cut.

9. A method for cutting bone, the method comprising:

accessing an image of the bone which is to be cut;

accessing an image of a pre-determined cutting pattern;

superimposing the image of the pre-determined cutting pattern against the image of the bone;

calculating the intersection of the pre-determined cutting pattern and the bone using the superimposed images of the pre-determined cutting pattern and the bone;

identifying a preferred surgical access prior to or during the surgery; and generating a tool path based upon the intersection of the pre-determined cutting pattern and the bone which accesses the bone through the preferred surgical access and leaves a thin perimeter of bone at the boundary of the bone cut is adjacent to a bone surface, except for where the tool needs to approach and cut the bone from the preferred surgical access;

wherein the tool path is generated to provide for tool access which complies with the surgical access which is defined by user input during the surgery; and wherein sizing of a surgical opening is reduced according to the following algorithm:
(1) Define a position, $P_0$, which is the center of the surgical opening:
(2) For a given tool position at a time t, let the tool center position be P(t) and let the directional vector of the long axis of the tool be V(t), then calculate distance d(t) as follows:

$$d(t)=|P_0-P(t)-(P_0-P(t))\cdot V(t)/|V(t)||$$

where the · means vector dot and | | means vector norm:
(3) The optimized tool path is that which minimizes the maximum d(t) over the entire time.

10. A method according to claim 9 further comprising cutting the bone according to the tool path generated.

11. A method according to claim 10 wherein the bone is cut by a surgical robot using the generated tool path.

12. A method according to claim 9 wherein the pre-determined cutting pattern is associated with an implant to be placed into the bone.

13. Apparatus for generating an improved tool path for cutting a bone so as to minimize soft tissue trauma, wherein the method comprises:
means for accessing an image of the bone which is to be cut;
means for accessing an image of a pre-determined cutting pattern;
means for superimposing the image of the pre-determined cutting pattern against the image of the bone;
means for calculating the intersection of the pre-determined cutting pattern and the bone using the superimposed images of the pre-determined cutting pattern and the bone;
means for generating a tool path based upon the intersection of the pre-determined cutting pattern and the bone so as to minimize soft tissue trauma by leaving a thin perimeter of bone at the boundary of the bone cut when the boundary of the bone cut is adjacent to a bone surface;
wherein the tool path is generated to provide for tool access which complies with the surgical access which is defined by user input during the surgery; and
wherein sizing of a surgical opening is reduced according to the following algorithm:
(1) Define a position, $P_0$, which is the center of the surgical opening:
(2) For a given tool position at a time t, let the tool center position be P(t) and let the directional vector of the long axis of the tool be V(t), then calculate distance d(t) as follows:

$$d(t)=|P_0-P(t)-(P_0-P(t))\cdot V(t)/|V(t)||$$

where the · means vector dot and | | means vector norm:
(3) The optimized tool path is that which minimizes the maximum d(t) over the entire time.

14. Apparatus according to claim 13 wherein the pre-determined cutting pattern is associated with an implant which is to be placed into the bone.

15. Apparatus for cutting bone, the apparatus comprising:
means for accessing an image of the bone which is to be cut;
means for accessing an image of a pre-determined cutting pattern;
means for superimposing the image of the pre-determined cutting pattern against the image of the bone;
means for calculating the intersection of the pre-determined cutting pattern and the bone using the superimposed images of the pre-determined cutting pattern and the bone;
means for identifying a preferred surgical access prior to or during the surgery; and
means for generating a tool path based upon the intersection of the pre-determined cutting pattern and the bone which accesses the bone through the preferred surgical access and leaves a thin perimeter of bone at the boundary of the bone cut is adjacent to a bone surface, except for where the tool needs to approach and cut the bone from the preferred surgical access;
wherein the tool path is generated to provide for tool access which complies with the surgical access which is defined by user input during the surgery; and
wherein sizing of a surgical opening is reduced according to the following algorithm:
(1) Define a position, $P_0$, which is the center of the surgical opening:
(2) For a given tool position at a time t, let the tool center position be P(t) and let the directional vector of the long axis of the tool be V(t), then calculate distance d(t) as follows:

$$d(t)=|P_0-P(t)-(P_0-P(t))\cdot V(t)/|V(t)||$$

where the · means vector dot and | | means vector norm:
(3) The optimized tool path is that which minimizes the maximum d(t) over the entire time.

16. Apparatus according to claim 15 further comprising means for cutting the bone according to the tool path generated.

17. Apparatus according to claim 16 wherein the bone is cut by a surgical robot using the generated tool path.

18. Apparatus according to claim 15 wherein the cutting pattern is associated with an implant to be placed into the bone.

* * * * *